(12) United States Patent
Lavoie et al.

(10) Patent No.: US 6,605,677 B2
(45) Date of Patent: Aug. 12, 2003

(54) OLEFIN POLYMERIZATION PROCESSES USING SUPPORTED CATALYSTS

(75) Inventors: Gino Georges Lavoie, Kingsport, TN (US); Peter Borden Mackenzie, Kingsport, TN (US); Christopher Moore Killian, Gray, TN (US); Thomas William Smith, Gainesville, FL (US)

(73) Assignee: Eastman Chemical Company, Kingsport, TN (US)

( * ) Notice: Subject to any disclaimer, the term of this patent is extended or adjusted under 35 U.S.C. 154(b) by 54 days.

(21) Appl. No.: 09/985,446

(22) Filed: Nov. 2, 2001

(65) Prior Publication Data

US 2002/0091210 A1 Jul. 11, 2002

Related U.S. Application Data

(63) Continuation-in-part of application No. 09/563,812, filed on May 3, 2000, which is a continuation-in-part of application No. 09/507,492, filed on Feb. 18, 2000.
(60) Provisional application No. 60/231,920, filed on Sep. 11, 2000, provisional application No. 60/246,254, filed on Nov. 6, 2000, provisional application No. 60/246,255, filed on Nov. 6, 2000, provisional application No. 60/246,178, filed on Nov. 6, 2000, and provisional application No. 60/303,150, filed on Jul. 6, 2001.

(51) Int. Cl.$^7$ .............................. C08F 4/70; B01J 31/38
(52) U.S. Cl. ...................... 526/161; 526/171; 526/172; 526/905; 502/155; 502/167
(58) Field of Search .............................. 526/171, 161, 526/172, 905; 502/155, 167

(56) References Cited

U.S. PATENT DOCUMENTS

| | | |
|---|---|---|
| 4,564,647 A | 1/1986 | Hayashi et al. |
| 4,724,273 A | 2/1988 | Fink et al. |
| 4,752,597 A | 6/1988 | Turner |
| 5,106,804 A | 4/1992 | Bailly et al. |
| 5,132,380 A | 7/1992 | Stevens et al. |
| 5,227,440 A | 7/1993 | Canich et al. |
| 5,296,565 A | 3/1994 | Ueda et al. |
| 5,324,800 A | 6/1994 | Welborn, Jr. et al. |
| 5,331,071 A | 7/1994 | Kataoka et al. |
| 5,332,706 A | 7/1994 | Nowlin et al. |
| 5,350,723 A | 9/1994 | Neithamer et al. |
| 5,399,635 A | 3/1995 | Neithamer et al. |
| 5,466,766 A | 11/1995 | Patsidis et al. |
| 5,468,702 A | 11/1995 | Jejelowo |
| 5,474,962 A | 12/1995 | Takahashi et al. |
| 5,578,537 A | 11/1996 | Hermann et al. |
| 5,863,853 A | 1/1999 | Vaughan et al. |
| 5,866,663 A | 2/1999 | Brookhart et al. |
| 5,880,241 A | 3/1999 | Brookhart et al. |
| 5,880,323 A | 3/1999 | Brookhart, III et al. |
| 5,886,224 A | 3/1999 | Brookhart et al. |
| 5,891,963 A | 4/1999 | Brookhart et al. |
| 6,197,715 B1 | 3/2001 | Bansleben et al. |
| 6,303,710 B1 * | 10/2001 | Xie .............................. 526/65 |

FOREIGN PATENT DOCUMENTS

| | | |
|---|---|---|
| DE | 19707236 A1 | 8/1998 |
| DE | 19944993 A1 | 7/1999 |
| DE | 19959251 A1 | 12/1999 |
| EP | 0 382 495 A2 | 8/1990 |
| EP | 0 416 815 A2 | 3/1991 |
| EP | 0 420 436 A1 | 4/1991 |
| EP | 0 532 098 A1 | 3/1993 |
| EP | 0 641 804 A2 | 3/1995 |
| EP | 0 816 384 A2 | 1/1998 |
| EP | 0 874 005 A1 | 10/1998 |
| EP | 0 884 331 A2 | 12/1998 |
| EP | 0 893 455 A1 | 1/1999 |
| EP | 1 099 714 A1 | 11/1999 |
| JP | 10-324709 | 3/1997 |
| JP | 9-255712 | 9/1997 |
| JP | 9-272709 | 10/1997 |
| JP | 9-272713 | 10/1997 |
| JP | 09/278822 | 10/1997 |
| WO | 94/01471 | 1/1994 |
| WO | 94/11410 | 5/1994 |
| WO | 94/14854 | 7/1994 |
| WO | 96/23010 | 8/1996 |
| WO | 97/02298 | 1/1997 |
| WO | 97/17380 | 5/1997 |
| WO | 97/38024 | 10/1997 |
| WO | 97/48735 | 12/1997 |
| WO | 97/48736 | 12/1997 |
| WO | 97/48737 | 12/1997 |
| WO | 97/48739 | 12/1997 |
| WO | 97/48740 | 12/1997 |
| WO | 97/48742 | 12/1997 |
| WO | 97/48777 | 12/1997 |
| WO | 98/03521 A | 1/1998 |
| WO | 98/03559 | 1/1998 |
| WO | 98/11144 | 3/1998 |
| WO | 98/27124 | 6/1998 |
| WO | 98/30609 | 7/1998 |
| WO | 98/30610 | 7/1998 |
| WO | 98/37110 | 8/1998 |
| WO | 98/40374 | 9/1998 |
| WO | 98/40420 | 9/1998 |
| WO | 98/40421 | 9/1998 |
| WO | 98/41529 | 9/1998 |
| WO | 98/42664 | 10/1998 |
| WO | 98/42665 | 10/1998 |
| WO | 98/47933 | 10/1998 |
| WO | 98/47934 | 10/1998 |
| WO | 98/56832 | 12/1998 |
| WO | 99/02472 | 1/1999 |
| WO | 99/02570 | 1/1999 |
| WO | 00/47592 A1 | 2/1999 |

(List continued on next page.)

*Primary Examiner*—Robert D. Harlan
(74) *Attorney, Agent, or Firm*—Jonathan D. Wood, Esq.; Bernard J. Graves, Jr., Esq.

(57) ABSTRACT

Improved Group 8–10 transition metal based supported catalyst processes for the polymerization of olefins are described. Some of the improvements pertain to protocols for catalyst preparation and activation which improve the catalyst productivity in the presence of hydrogen as a molecular weight control agent.

7 Claims, 2 Drawing Sheets

FOREIGN PATENT DOCUMENTS

| | | |
|---|---|---|
| WO | 99/05189 | 2/1999 |
| WO | 99/09078 | 2/1999 |
| WO | 00/58320 A1 | 3/1999 |
| WO | 99/10391 | 3/1999 |
| WO | 99/12981 | 3/1999 |
| WO | 01/07491 A1 | 7/1999 |
| WO | 01/12684 A1 | 8/1999 |
| WO | 01/07492 A1 | 9/1999 |
| WO | 01/14391 A1 | 9/1999 |
| WO | 01/21586 A1 | 9/1999 |
| WO | 01/23396 A1 | 9/1999 |
| WO | 01/42257 A1 | 12/1999 |
| WO | 99/62968 A | 12/1999 |
| WO | 00/04057 | 1/2000 |
| WO | 01/55231 A1 | 1/2000 |
| WO | 00/32641 A | 6/2000 |
| WO | 00/50470 A | 8/2000 |
| WO | 01/92342 A | 12/2001 |

OTHER PUBLICATIONS

Timo Repo, et al., "Ethylenebis(Salicylidenetiminato)zirconium Dichloride: Crystal Structure and Use as a Heterogeneous Catalyst in the Polymerization of Ethylene," *Maromolecules*, (1997), 171–175, 30.

Oleg V. Mikhailov, "From Novel Complexing Conditions to Novel Coordination Compounds of Nickel (II) with Dithiooxamide and its Bulky Analogues," *Transition Met. Chem.*, (1996), 363–369, 21.

A. Bach, et al., "Metal Chelates of N–(1–Pyrrolyl)salicylaldimines and Their Structure Determination by X–Ray Structure Analysis and X–Ray Absorption Spectroscopy (Xanes)," *Z. Naturforsch., Chem. Sci.*, 1996, pp. 757–764, vol. 51(6).

A. V. Bordunov, et al., "Azacrown Ethers Containing Oximic and Schiff Base Sidearms—Potential Heteronuclear Metal Ion Receptors," *Tetrahedron, NL*, Dec. 29, 1997, pp. 17595–17606, vol. 53, No. 52, Elsevier Science Publishers, Amsterdam.

M. Brookhart et al., *J. Am. Chem. Soc.*, 1995, pp. 6414–6415, 117.

Buelow, "Chemische Bericht," *Berichte Der Deutschen Chemischen Gesellschaft, DE, Verlag Chemie. Weinheim*, 1905, pp. 3915, 3917, vol. 38.

R. M. Claramunt, et al., "Rhodium (I) Complexes with the Polydentate Ligand 3,5–bis(4–methylpyrazol–1–yl)–4–methylpyrazole," *Journal Organometallic Chemistry*, 1991, pp. 259–271, vol. 412, No. 1–2.

I. O. Fritsky, et al., "Template Synthesis of Square–Planar Nickel (II) and Copper (III) Complexes Based on Hydrazide Ligands," *J. Chem. Soc., Dalton Trans.*, 1998, pp. 3269–3274, vol. 19.

V. C. Gibson et al., *Chem. Commun.*, 1998, pp. 313–314.

S. D. Ittel et al., "Late–Metal Catalysts for Ethylene Homo– and Copolymerization," *Chem. Rev.*, 2000, pp. 1169–1203, 100.

W. Keim et al., *Angew Chem. Int. Ed. Engl.*, 1981, pp. 116–117, 20.

D. H. McConville et al., *J. Am. Chem. Soc.*, 1996, pp. 10008–10009, 118.

V. M. Mohring et al., *Agnew. Chem. Int. Ed. Engl.*, 1985, pp. 1001–1003, 24.

K. K. Narang, et al., Glyoxal–Aroyl Hydrazone (Schiff Base) Complexes of Nickel (II), Copper (II) & Zinc (II), *Indian J. Chem.*, Sect. A., 1982, pp. 830–832, vol. 21A(8).

K. K. Narang, et al., "Synthesis, Characterization, Thermal Studies and Biological Activity of Iron (III) Complexes with Some Acylhydrazines," *Synth. React. Inorg. Met.–Org. Chem.*, 1993, pp. 971–989, vol. 23(6).

F. A. Neugebauer, "ESR Studies of 1,2,4,5–Tetraazapentenyls," *Chem. Ber.*, 1973, pp. 1716–1723, vol. 106(6).

M. Peuckert et al., *Organometallics*, 1983, pp. 594–597, 2.

S. B. Roscoe et al., "Polyolefin Spheres from Metallocenes Supported on Noninteracting Polystyrene," *Science*, 1998, pp. 270–273, 280.

L. Rosenberg, et al., "Binuclear Nickel (II) and Cobalt (II) Complexes of the Novel Binucleating Ligand 3,–Bis(1'–pyrazolyl)pyridazine. Crystal and Molecular Structure and Magnetism of Bis[$\mu$–3, 6–bis(1'–pyrazolyl)pyridazine–$N^1(Ni^1)N^{2'}(Ni^1)N^{2'}(Ni^1)N^2(Ni^2)N^{2''}(Ni^{2'})$]–bis[diaquanickel {II}] Tetrachloride Dihydrate," *J. Chem. Soc., Dalton Trans.*, 1986, pp. 625–631, vol. 3.

M. Schmid et al., "New $C_{2V}$ and Chiral $C_2$–Symmetric Olefin Polymerization Catalysts Based on Nickel (II) and Palladium (II) Diimine Complexes Bearing 2,6–Diphenyl Aniline Moieties: Synthesis, Structural Characterization, and First Insight into Polymerization Properties," *Organometallics*, 2001, 20(11), 2321.

R. R. Schrock et al., *J. Am. Chem. Soc.*, 1997, pp. 3830–3831, 119.

R. R. Schrock et al., *J. Am. Chem. Soc.*, 1999, pp. 5797–5798, 121.

S. H. Strauss, *Chem. Rev.*, 1993, pp. 927–942, 93.

A. A. Watson, et al., "Chiral Heterocyclic Ligands. VIII. Syntheses and Complexes of New Chelating Ligands Derived from Camphor," *Aust. J. Chem.*, 1995, pp. 1549–1572, vol. 48, No. 9.

\* cited by examiner

OLEFIN POLYMERIZATION PROCESSES USING SUPPORTED CATALYSTS

CROSS REFERENCE TO RELATED APPLICATIONS

This application claims the benefit of the following applications under 35 USC §120: C-I-P of application Ser. No. 09/563,812, filed May 3, 2000, and which is a C-I-P application Ser. No. 09/507,492, filed Feb. 18, 2000, the entire contents of which are incorporated herein by reference; and the benefit of the following applications under 35 USC §119: Provisional Application No. 60/231,920, filed Sep. 11, 2000; Provisional Application No. 60/246,254, filed Nov. 6, 2000; Provisional Application No. 60/246,255, filed Nov. 6, 2000; Provisional Application No. 60/246,178, filed Nov. 6, 2000; and Provisional Application No. 60/303,150, filed Jul. 6, 2001, the entire contents of which are incorporated herein by reference.

FIELD OF THE INVENTION

This application generally relates to olefin polymerization catalyst compositions and olefin polymerization processes using the same.

BACKGROUND OF THE INVENTION

The use of late transition metal complexes as catalysts for olefin polymerization has recently been reviewed by Ittel et al. (*Chem. Rev.* 2000, 100, 1169). Late transition metal catalysts have also been described in WO 01/07492, WO 01/55231, WO 01/42257, WO 01/21586, and *Organometallics* 2001, 20, 2321. Notwithstanding the developments described therein, there remains a need for new late transition metal catalysts and processes with improved productivities under commercial reactor operating conditions, especially those involving gas phase processes. New catalysts and processes for these purposes are described herein.

SUMMARY OF THE INVENTION

Gas phase processes represent a large fraction of current worldwide polyethylene production, and generally involve the use of hydrogen to control the polymer molecular weight. Although many nickel catalysts are severely inhibited by added hydrogen, we have previously described, in U.S. patent application Ser. No. 09/507,492, filed Feb. 18, 2000, U.S. patent application Ser. No. 09/563,812, filed May 3, 2000, and U.S. patent application Ser. No. 09/231,920, filed Sep. 11, 2000, preferred classes of nickel catalysts that exhibit little or no loss of catalytic activity in homogeneously initiated, solution or slurry phase reactions conducted in the presence of hydrogen. We have, however, unexpectedly observed that these same, otherwise hydrogen-tolerant catalysts frequently exhibit an inappropriate response to hydrogen in supported catalyst gas phase polymerizations, in that much poorer productivities are observed when ethylene polymerizations are carried out in the presence of hydrogen, compared to similar reactions without hydrogen. In an effort to solve this problem, we have surprisingly discovered that treating the support with a pore-filling agent, either before, during, or after the catalyst and the support have been combined, can significantly improve the catalyst productivity in the presence of hydrogen. Pore-filling agents suitable for use in the present invention include materials that are: (a) compatible with the desired catalysis, by which we mean the pore-filling agent either does not interfere with the desired catalysis, or acts to usefully modify the catalyst activity or selectivity, and (b) (i) low in volatility, by which we mean the pore-filling agent is either sufficiently non-volatile that not all of it is lost before the catalyst is introduced into the olefin polymerization reactor and olefin polymerization is initiated, and enough remains to improve the catalyst productivity in the presence of hydrogen, or (ii) relatively more volatile, but the treated supported catalyst can be handled in such a way that a sufficient amount of the pore-filling agent remains when the supported catalyst is exposed to hydrogen that improved productivity is observed in the presence of hydrogen. Examples of such pore-filling agents include, but are not limited to, triethylborane, diethylzinc, triethylaluminum, xylene, and triphenylmethane.

We have also discovered that activating supported Group 8–10 metal catalysts in the presence of one or more olefins, but in the absence of hydrogen, can also result in significantly improved productivities upon subsequent exposure to hydrogen. We have further discovered that improved productivities in the presence of hydrogen can also be achieved by activating the supported Group 8–10 metal catalysts at high partial pressures of ethylene. By "high partial pressures of ethylene", we mean partial pressures of at least 400 psig, preferably at least 600 psig.

These discoveries are both surprising and unexpected because the art did not teach either the problem of decreased productivity of supported catalysts based on cationic nickel complexes of bidentate ligands that are exposed to hydrogen during gas phase polymerization or a solution to the problem, e.g., the use of certain pore-filling agents, the controlled exposure to hydrogen, or the control of the ethylene partial pressure during catalyst activation.

Although it is recognized that the above-mentioned treatment of the support may result in both chemical and physical modifications of the supported catalysts, we believe, without wishing to be bound by theory, that the pore-filling agent may be acting to affect the relative concentrations of key reactants at the site of the Group 8–10 metal catalyst during activation, either by acting as a physical barrier to diffusion or by virtue of the different solubilities of the key reagents in the pore-filling agent. In particular, we believe that the pore-filling agent acts to raise the relative concentration of ethylene to hydrogen at the active site at the time of activation. Activating the catalyst in the presence of olefin, but in the absence of hydrogen, may result in a similar effect wherein the polymer itself serves to modify the relative concentrations of key reagents. In addition to the concentration of hydrogen and olefin, the concentration of the co-catalyst(s) and the concentration of the catalyst itself may also be usefully modified through the use of the specified pore-filling agents. Activating the catalyst in the presence of hydrogen at relatively high partial pressures of ethylene may also result in improved catalyst productivity in the presence of hydrogen for the same reason. Without wishing to be bound by theory, we believe that it is important that the activated catalyst react with ethylene or another olefin before it reacts with hydrogen.

Thus, in a first aspect, this invention pertains to an improved process for the polymerization of olefins, comprising: contacting one or more olefins with a catalyst comprising a Group 8–10 transition metal complex of a bidentate N,N—, N,O—, N,P—, or P,P-donor ligand, wherein the catalyst is attached to a solid support, wherein the solid support has been treated with a pore-filling agent, either before, during, or after the catalyst and the support have been combined, wherein the pore-filling agent is introduced into the pores of the support either as a pure liquid or as a solution in a suitable solvent. By "suitable solvent", we mean a solvent that (a) is itself a useful supported catalyst pore-filling agent, (b) is readily removed prior to polymerization, or (c) is compatible with the process and does not inhibit the catalyst, unless any such inhibition is modest and advantageous in the context of the process, as would be the case, for example, if the catalyst activated more slowly and thereby reduce a tendency for particle overheating in a gas phase reactor. Such overheating can lead to particle agglomeration and reactor fouling.

In a first preferred embodiment, the ligand is selected from Set 1;

wherein:
$R^{2x,y}$ are each independently H, hydrocarbyl, substituted hydrocarbyl, heteroatom connected hydrocarbyl, heteroatom connected substituted hydrocarbyl, silyl, or ferrocenyl; in addition, $R^{2x}$ and $R^{2y}$ may be linked by a bridging group;
$R^{3a-l}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; and
$R^{4a,b}$ are each independently hydrocarbyl, substituted hydrocarbyl, heteroatom connected hydrocarbyl, or heteroatom connected substituted hydrocarbyl; in addition, $R^{4a}$ and $R^{4b}$ may be linked by a bridging group.

In a second preferred embodiment, the catalyst comprises a nickel complex of a bidentate N,N-donor ligand, wherein the N-donor atoms are substituted by aromatic or heteroaromatic rings, wherein the ortho positions of the rings are substituted by bromo, trifluoromethyl, fluoroalkyl, aryl, or heteroaryl groups.

In a third preferred embodiment, at least 20%, more preferably at least 40%, even more preferably at least 60%, of the remaining pore volume of the supported catalyst is filled by the pore-filling agent. By "remaining pore volume", we mean the pore volume of the support minus the volume occupied by the catalyst and any co-catalyst.

In a second aspect, this invention relates to a process for the polymerization of olefins, comprising: contacting one or more olefins with a catalyst comprising a Group 8–10 transition metal complex of a bidentate N,N—, N,O—, N,P—, or P,P-donor, wherein the catalyst is attached to a solid support and wherein the catalyst is first activated in the absence of hydrogen in a first reactor containing one or more olefins, and then introduced into a second reactor containing hydrogen in which the bulk of the polymerization takes place.

In a first preferred embodiment of this second aspect, the process comprises a nickel complex of a bidentate N,N-donor ligand, wherein the N-donor atoms are substituted by aromatic or heteroaromatic rings, wherein the ortho positions of the rings are substituted by bromo, trifluoromethyl, fluoroalkyl, aryl, or heteroaryl groups.

In a second preferred embodiment of this second aspect, the ligand is selected from Set 2;

Set 2 wherein:

$R^{2x,y}$ are each independently H, hydrocarbyl, substituted hydrocarbyl, heteroatom connected hydrocarbyl, heteroatom connected substituted hydrocarbyl, silyl, or ferrocenyl; in addition, $R^{2x}$ and $R^{2y}$ may be linked by a bridging group;

$R^{3a-l}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; and $R^{4a,b}$ are each independently hydrocarbyl, substituted hydrocarbyl, heteroatom connected hydrocarbyl, or heteroatom connected substituted hydrocarbyl; in addition, $R^{4a}$ and $R^{4b}$ may be linked by a bridging group.

In a fourth preferred embodiment of this second aspect, two or three of the ortho positions of the rings are substituted by aryl or heteroaryl groups, and the remainder of the ortho positions are substituted by bromo, trifluoromethyl, or fluoroalkyl groups.

In a third aspect, this invention relates to a process for the polymerization of olefins, comprising: contacting one or more olefins with a catalyst comprising a Group 8–10 transition metal complex of a bidentate N,N—, N,O—, N,P—, or P,P-donor, wherein the catalyst is attached to a solid support, and wherein the catalyst is first activated in the presence of hydrogen at a partial pressure of ethylene greater than 400 psig.

In a first preferred embodiment of this third aspect, the partial pressure of ethylene is at least 600 psig.

DETAILED DESCRIPTION OF THE INVENTION

In this disclosure, symbols ordinarily used to denote elements in the Periodic Table and commonly abbreviated groups, take their ordinary meaning, unless otherwise specified. Thus, N, O, S, P, and Si stand for nitrogen, oxygen, sulfur, phosphorus, and silicon, respectively, while Me, Et, Pr, $^i$Pr, Bu, $^t$Bu and Ph stand for methyl, ethyl, propyl, iso-propyl, butyl, tert-butyl and phenyl, respectively.

A "1-pyrrolyl or substituted 1-pyrrolyl" group refers to a group of formula II below:

II wherein $R^{3a-d}$ are each independently H, hydrocarbyl, substituted hydrocarbyl, heteroatom connected hydrocarbyl, heteroatom connected substituted hydrocarbyl, fluoroalkyl, silyl, boryl, fluoro, chloro, bromo, cyano, or nitro; in addition, any two or more of $R^{3a-d}$ may be linked by a bridging group or groups to form bicyclic or polycyclic ring systems including carbazol-9-yl and indol-1-yl.

A "hydrocarbyl" group means a monovalent or divalent, linear, branched, or cyclic group which contains only carbon and hydrogen atoms. Examples of monovalent hydrocarbyls include the following: $C_1$–$C_{20}$ alkyl; $C_1$–$C_{20}$ alkyl substituted with one or more groups selected from $C_1$–$C_{20}$ alkyl, $C_3$–$C_8$ cycloalkyl, and aryl; $C_3$–$C_8$ cycloalkyl; $C_3$–$C_8$ cycloalkyl substituted with one or more groups selected from $C_1$–$C_{20}$ alkyl, $C_3$–$C_8$ cycloalkyl, and aryl; $C_6$–$C_{14}$ aryl; and $C_6$–$C_{14}$ aryl substituted with one or more groups selected from $C_1$–$C_{20}$ alkyl, $C_3$–$C_8$ cycloalkyl, and aryl. Examples of divalent (bridging) hydrocarbyls include: —$CH_2$—, —$CH_2CH_2$—, —$CH_2CH_2CH_2$—, and 1,2-phenylene.

The term "aryl" refers to an aromatic carbocyclic monoradical, which may be substituted or unsubstituted, wherein the substituents are halo, hydrocarbyl, substituted hydrocarbyl, heteroatom attached hydrocarbyl, heteroatom attached substituted hydrocarbyl, nitro, cyano, fluoroalkyl, sulfonyl, and the like. Examples include: phenyl, naphthyl, anthracenyl, phenanthracenyl, 2,6-diphenylphenyl, 3,5-dimethylphenyl, 4-nitrophenyl, 3-nitrophenyl, 4-methoxyphenyl, 4-dimethylaminophenyl, 2,6-dibromophenyl, 2,4,6-tribromophenyl, 2,4-dibromo-6-phenylphenyl, 2,6-di(4-tert-butylphenyl)phenyl, 2,6-di(4-tert-butylphenyl)-4-phenylphenyl, 2,6-di(4-phenylphenyl)-4-phenylphenyl, 2,4-dibromo-6-trifluoromethylphenyl, 2,4-bis(4-tert-butylphenyl)-6-trifluoromethylphenyl, 2-chloro-4,6-di(4-tert-butylphenyl)phenyl, 2,6-di(1-naphthyl)-4-phenylphenyl, and the like.

A "heterocyclic ring" refers to a carbocyclic ring wherein one or more of the carbon atoms has been replaced by an atom selected from the group consisting of O, N, S, P, Se, As, Si, B, and the like.

A "heteroaromatic ring" refers to an aromatic heterocyclic ring; examples include pyrrole, furan, thiophene, indene, imidazole, oxazole, isoxazole, carbazole, thiazole, pyrimidine, pyridine, pyridazine, pyrazine, benzothiophene, and the like.

A "heteroaryl" refers to a heterocyclic monoradical which is aromatic; examples include 1-pyrrolyl, 2-pyrrolyl, 3-pyrrolyl, furyl, thienyl, indenyl, imidazolyl, oxazolyl, isoxazolyl, carbazolyl, thiazolyl, pyrimidinyl, pyridyl, pyridazinyl, pyrazinyl, benzothienyl, and the like, and substituted derivatives thereof.

A "silyl" group refers to a $SiR_3$ group wherein Si is silicon and R is hydrocarbyl, substituted hydrocarbyl, heteroatom connected hydrocarbyl, or silyl, as in $Si(SiR_3)_3$.

A "boryl" group refers to a $BR_2$ or $B(OR)_2$ group, wherein R is hydrocarbyl or substituted hydrocarbyl.

A "heteroatom" refers to an atom other than carbon or hydrogen. Preferred heteroatoms include oxygen, nitrogen, phosphorus, sulfur, selenium, arsenic, chlorine, bromine, silicon, and fluorine.

A "substituted hydrocarbyl" refers to a monovalent, divalent, or trivalent hydrocarbyl substituted with one or more heteroatoms. Examples of monovalent substituted hydrocarbyls include: 2,6-dimethyl-4-methoxyphenyl, 2,6-diisopropyl-4-methoxyphenyl, 4-cyano-2,6-dimethylphenyl, 2,6-dimethyl-4-nitrophenyl, 2,6-difluorophenyl, 2,6-dibromophenyl, 2,6-dichlorophenyl, 4-methoxycarbonyl-2,6-dimethylphenyl, 2-tert-butyl-6-chlorophenyl, 2,6-dimethyl-4-phenylsulfonylphenyl, 2,6-dimethyl-4-trifluoromethylphenyl, 2,6-dimethyl-4-trimethylammoniumphenyl (associated with a weakly coordinated anion), 2,6-dimethyl-4-hydroxyphenyl, 9-hydroxyanthr-10-yl, 2-chloronapth-1-yl, 4-methoxyphenyl, 4-nitrophenyl, 9-nitroanthr-10-yl, —$CH_2OCH_3$, cyano, trifluoromethyl, and fluoroalkyl. Examples of divalent (bridging) substituted hydrocarbyls include: 4-methoxy-1,2-phenylene, 1-methoxymethyl-1,2-ethanediyl, 1,2-bis(benzyloxymethyl)-1,2-ethanediyl, and 1-(4-methoxyphenyl)-1,2-ethanediyl.

A "heteroatom connected hydrocarbyl" refers to a group of the type $E^{10}$(hydrocarbyl), $E^{20}$H(hydrocarbyl), or $E^{20}$(hydrocarbyl)$_2$, where $E^{10}$ is an atom selected from Group 16 and $E^{20}$ is an atom selected from Group 15. A "heteroatom connected substituted hydrocarbyl" refers to a group of the type $E^{10}$(substituted hydrocarbyl), $E^{20}$H(substituted hydrocarbyl), or $E^{20}$(substituted hydrocarbyl)$_2$, where $E^{10}$ is an atom selected from Group 16 and $E^{20}$ is an atom selected from Group 15.

The term "fluoroalkyl" as used herein refers to a $C_1$–$C_{20}$ alkyl group substituted by one or more fluorine atoms.

An "olefin" refers to a compound of the formula $R^{1a}CH{=}CHR^{1b}$, where $R^{1a}$ and $R^{1b}$ may independently be H, hydrocarbyl, substituted hydrocarbyl, fluoroalkyl, silyl, O(hydrocarbyl), or O(substituted hydrocarbyl), and where $R^{1a}$ and $R^{1b}$ may be connected to form a cyclic olefin, provided that in all cases, the substituents $R^{1a}$ and $R^{1b}$ are compatible with the catalyst. In the case of most Group 4–7 catalysts, this will generally mean that the olefin should not contain good Lewis base donors, since this will tend to severely inhibit catalysis. Preferred olefins for such catalysts include ethylene, propylene, butene, hexene, octene, cyclopentene, norbornene, and styrene. In the case of the Group 8–10 catalysts, Lewis basic substituents on the olefin will tend to reduce the rate of catalysis in most cases; however, useful rates of homopolymerization or copolymerization can nonetheless be achieved with some of those olefins. Preferred olefins for such catalysts include ethylene, propylene, butene, hexene, octene, and fluoroalkyl substituted olefins, but may also include, in the case of palladium and some of the more functional group tolerant nickel catalysts, norbornene, substituted norbornenes (e.g., norbornenes substituted at the 5-position with halide, siloxy, silane, halo carbon, ester, acetyl, alcohol, or amino groups), cyclopentene, ethyl undecenoate, acrylates, vinyl ethylene carbonate, 4-vinyl-2,2-dimethyl-1,3-dioxolane, and vinyl acetate.

In some cases, the Group 8–10 catalysts can be inhibited by olefins which contain additional olefinic or acetylenic functionality. This is especially likely if the catalyst is prone to "chain-running" wherein the catalyst can migrate up and down the polymer chain between insertions, since this can lead to the formation of relatively unreactive π-allylic intermediates when the olefin monomer contains additional unsaturation. Such effects are best determined on a case-by-case basis, but may be predicted to some extent through knowledge of how much branching is observed with a given catalyst in ethylene homopolymerizations; those catalysts which tend to give relatively high levels of branching with ethylene will tend to exhibit lower rates when short chain diene co-monomers are used under the same conditions. Longer chain dienes tend to be less inhibitory than shorter chain dienes, when other factors are kept constant, since the catalyst has to migrate farther to form the π-allyl, and another insertion may intervene first. Similar considerations apply to unsaturated esters which are capable of inserting and chain-running to form relatively stable intramolecular chelate structures wherein the Lewis basic ester functionality occupies a coordination site on the catalyst. In such cases, short chain unsaturated esters, such as methyl acrylate, tend to be more inhibitory than long chain esters, such as ethyl undecenoate, if all other factors are kept constant.

The term "ortho" is used to refer to substituents attached to the 2- and 6-positions of a 1-attached, six-membered aromatic or heteroaromatic ring, or the 2- and 5-positions of a 1-attached, five-membered aromatic or heteroaromatic ring, or more generally the first substitutable positions on either side of the point of attachment of the aromatic or heteroaromatic ring to the donor nitrogen.

By "chain running", we mean the process by which certain olefin polymerization catalysts, especially those based on Group 8–10 transition metal complexes of bidentate ligands, are capable of migrating along a growing polymer chain between insertion events to form branched polymers from ethylene alone, and give modes of enchainment other than 1,2 enchainment when substituted alkenes are polymerized or copolymerized.

By "higher productivities in the presence of hydrogen", we mean a catalyst productivity, expressed in units of kg polymer per mmole catalyst, which is at least 25% higher, preferably 50% higher, even more preferably 100% higher than that observed under the same conditions using an otherwise similar supported catalyst which has not been treated as described in the first, second, or third aspects of this invention.

By "in the presence of hydrogen", we mean an amount of hydrogen sufficient to reduce the number average molecular weight of the polymer by at least 5%, preferably at least 10%, even more preferably at least 20%, relative to an otherwise similar reaction conducted in the absence of hydrogen.

A "π-allyl" group refers to a monoanionic group with three $sp^2$ carbon atoms bound to a metal center in a $\eta^3$-fashion. Any of the three $sp^2$ carbon atoms may be substituted with a hydrocarbyl, substituted hydrocarbyl, heteroatom connected hydrocarbyl, heteroatom connected substituted hydrocarbyl, or O-silyl group.

Examples of π-allyl groups include:

The term π-benzyl group denotes a π-allyl group where two of the $sp^2$ carbon atoms are part of an aromatic ring. Examples of π-benzyl groups include:

A "bridging group" refers to an atom or group which links two or more groups, which has an appropriate valency to satisfy its requirements as a bridging group, and which is compatible with the desired catalysis. Suitable examples include divalent or trivalent hydrocarbyl, substituted hydrocarbyl, heteroatom connected hydrocarbyl, heteroatom connected substituted hydrocarbyl, substituted silicon (IV), boron(III), N(III), P(III), and P(V), —C(O)—, —SO$_2$—, —C(S)—, —B(OMe)—, —C(O)C(O)—, O, S, and Se. In some cases, the groups which are said to be "linked by a bridging group" are directly bonded to one another, in which case the term "bridging group" is meant to refer to that bond.

By "compatible with the desired catalysis," we mean the bridging group either does not interfere with the desired catalysis, or acts to usefully modify the catalyst activity or selectivity.

The term "weakly coordinating anion" is well known in the art per se and generally refers to a large bulky anion capable of delocalization of the negative charge of the anion. The importance of such delocalization depends to some extent on the nature of the transition metal comprising the cationic active species, with the Group 4–6 transition metals requiring less coordinating anions, such as $B(C_6F_5)_4^-$, than many Group 8–10 transition metal based catalysts, which can in some cases give active catalysts with $BF_4^-$ counteranions. Weakly coordinating anions, not all of which would be considered bulky, include, but are not limited to: $B(C_6F_5)_4^-$, $PF_6^-$, $BF_4^-$, $SbF_6^-$, $(F_3CSO_2)_2N^-$, $(F_3CSO_2)_3C^-$, $OS(O)_2CF_3^-$, $(Ph)_4B^-$, and $Ar_4B^-$ wherein $Ar_4B^-$=tetrakis[3,5-bis(trifluoromethyl)phenyl]-borate. The weakly coordinating nature of such anions is known and described in the literature (S. Strauss et al., Chem. Rev., 1993, 93, 927).

The abbreviation "acac" refers to acetylacetonate. In general, substituted acetylacetonates, wherein one or more hydrogens in the parent structure have been replaced by a hydrocarbyl, substituted hydrocarbyl, or fluoroalkyl, may be used in place of the "acac". Hydrocarbyl substituted acetylacetonates may be preferred in some cases when it is important, for example, to improve the solubility of a (ligand)Ni(acac)BF$_4$ salt in mineral spirits.

By "under the same reaction conditions", we mean the catalyst loading, solvent, solvent volume, agitation, ethylene pressure, co-monomer concentration, reaction time, and other process relevant parameters are sufficiently similar that a valid comparison can be made between two catalysts.

The phrase "one or more olefins" refers to the use of one or more chemically different olefin monomer feedstocks, for example, ethylene and propylene.

A variety of protocols may be used to generate active polymerization catalysts comprising transition metal complexes of various nitrogen, phosphorous, oxygen and sulfur donor ligands. Examples include (i) the reaction of a Group 4 metallocene dichloride with MAO, (ii) the reaction of a Group 4 metallocene dimethyl complex with N,N-diethylanilinium tetrakis(pentafluorophenyl)borate, (iii) the reaction of a Group 8 or 9 metal dihalide complex of a tridentate N-donor ligand with an alkylaluminum reagent, (iv) the reaction of a Group 8 or 9 metal dialkyl complex of a tridentate N-donor ligand with MAO or HB(3,5-bis(trifluoromethyl)phenyl)$_4$, (v) the reaction of $(Me_2N)_4Zr$ with 2 equivalents of an N-pyrrol-1-ylsalicylimine, followed by treatment of the product of that reaction with Me$_3$SiCl and then a triisobutylaluminum-modified methylaluminoxane, and (vi) the reaction of a nickel or palladium dihalide complex of a bidentate N-donor ligand with an alkylaluminum reagent. Additional methods described herein include the reaction of (tridentate N-donor ligand)M(acac)B(C$_6$F$_5$)$_4$ salts with an alkylaluminum reagent, where M is Fe(II) or Co(II), and the reaction of (bidentate N-donor ligand)Ni(acac)X salts with an alkylaluminum reagent, where X is a weakly coordinating anion, such as $B(C_6F_5)_4^-$, $BF_4^-$, $PF_6^-$, $SbF_6^{--}$, $(F_3CSO_2)_2N^-$, $(F_3CSO_2)_3C^-$, and $OS(O)_2CF_3^-$. Cationic [(ligand)M(π-allyl)]$^+$ complexes with weakly coordinating counteranions, where M is a Group 10 transition metal, are often also suitable catalyst precursors, requiring only exposure to olefin monomer and in some cases elevated temperatures (40–100° C.) or added Lewis acid, or both, to form an active polymerization catalyst.

More generally, a variety of (ligand)$_n$M(Z$^{1a}$)(Z$^{1b}$) complexes, where "ligand" refers to a compound of the present invention, n is 1 or 2, M is a Group 8–10 transition metal, and Z$^{1a}$ and Z$^{1b}$ are univalent groups, or may be taken together to form a divalent group, may be reacted with one or more compounds, collectively referred to as compound Y, which function as co-catalysts or activators, to generate an active catalyst of the form [(ligand)$_n$M(T$^{1a}$)(L)]$^+$X$^-$, where n is 1 or 2, T$^{1a}$ is a hydrogen atom or hydrocarbyl, L is an olefin or neutral donor group capable of being displaced by an olefin, M is a Group 4–10 transition metal, and X is a weakly coordinating anion. When Z$^{1a}$ and Z$^{1b}$ are both halide, examples of compound Y include: methylaluminoxane (herein MAO) and other aluminum sesquioxides, R$_3$Al, R$_2$AlCl, and RAlCl$_2$ (wherein R is alkyl, and plural groups R may be the same or different). When Z$^{1a}$ and Z$^{1b}$ are both alkyl, examples of a compound Y include: MAO and other aluminum sesquioxides, R$_3$Al, R$_2$AlCl, RAlCl$_2$ (wherein R is alkyl, and plural groups R may be the same or different), B(C$_6$F$_5$)$_3$, R$^0{}_3$Sn[BF$_4$] (wherein R$^0$ is hydrocarbyl or substituted hydrocarbyl and plural groups R$^0$ may be the same or different), H$^+$X$^-$, wherein X$^-$ is a weakly coordinating anion, for example, tetrakis[3,5-bis(trifluoromethyl)phenyl]borate, and Lewis acidic or Brønsted acidic metal oxides, for example, montmorillonite clay. In some cases, for example, when Z$^{1a}$ and Z$^{1b}$ are both halide or carboxylate, sequential treatment with a metal hydrocarbyl, followed by reaction with a Lewis acid, may be required to generate an active catalyst. Examples of metal hydrocarbyls include: MAO, other aluminum sesquioxides, R$_3$Al, R$_2$AlCl, RAlCl$_2$ (wherein R is alkyl, and plural groups R may be the same or different), Grignard reagents, organolithium reagents, and diorganozinc reagents. Examples of Lewis acids include: MAO, other aluminum sesquioxides, R$_3$Al, R$_2$AlCl, RAlCl$_2$ (wherein R is alkyl, and plural groups R may be the same or different), B(C$_6$F$_5$)$_3$, R$^0{}_3$Sn[BF$_4$] (wherein R$^0$ is hydrocarbyl or substituted hydrocarbyl and plural groups R$^0$ may be the same or different), and Lewis acidic metal oxides.

The term "alkylaluminum" is used to refer to compounds containing at least one alkyl group bonded to Al(III), which are capable of reacting with a metal complex of the present invention to generate an active olefin polymerization catalyst. In general, this will involve exchanging one or more alkyl groups from the aluminum with a monoanionic atom or group on the metal complex procatalyst. In some cases, a hydride may be directly transferred from the β-carbon of the aluminum alkyl to the metal complex. Subsequent abstraction of a second monoanionic atom or group from the metal complex may also be required to generate a cationic active catalyst. When the pro-catalyst is already a cationic metal complex, the role of the alkylaluminum may simply be to exchange an alkyl or hydride from the aluminum with a monoanionic group, such as acetylacetonate, attached to the metal complex. In the case of a cationic π-allyl or π-benzyl pro-catalyst, the alkylaluminum reagent may, in some cases, simply act as a Lewis acid, to promote conversion of the π-allyl or π-benzyl to a σ-allyl or σ-benzyl bonding mode, thereby facilitating binding and insertion of the olefin monomer. When a cationic pro-catalyst is used with an alkylaluminum activator or co-catalyst, it should also be recognized that the starting counteranion (e.g. BF$_4^-$) may react with the alkylaluminum reagent to generate a new counteranion (or a mixture of several different counteranions) under olefin polymerization reaction conditions. Examples of alkylaluminum reagents include: MAO, other aluminum sesquioxides, Me$_3$Al, EtAlCl$_2$, Et$_2$AlCl, R$_3$Al, R$_2$AlCl, RAlCl$_2$ (wherein R is alkyl, and plural groups R may be the same or different), and the like.

The foregoing discussion is intended to illustrate that there are frequently many ways to generate an active catalyst. There are a variety of methods wherein the ligands of the present invention can be reacted with a suitable metal precursor, and optionally a co-catalyst, to generate an active olefin polymerization catalyst. Without wishing to be bound by theory, we believe that the active catalyst typically comprises the catalytically active metal, one or more ligands of the present invention, the growing polymer chain (or a hydride capable of initiating a new chain), and a site on the metal adjacent to the metal-alkyl bond of the chain where ethylene can coordinate, or at least closely approach, prior to insertion. Where specific structures for active catalysts have been implied herein, it should be understood that an that active catalysts comprising the ligands of the present invention are formed as the reaction products of the catalyst activation reactions disclosed herein, regardless of the detailed structures of those active species.

Active catalysts may, in some cases, be generated from more than one oxidation state of a given metal. For example, the present invention describes the use of both Co(III) and Co(II) catalyst precursors to effect olefin polymerization using MAO or other alkylaluminum co-catalysts. Where only one oxidation state of a given metal has been specified herein, it is therefore to be understood that other oxidation states of the same metal, complexed by the ligands of the present invention, can serve as catalyst precursors or active catalysts. When different oxidation state complexes of the ligands are used, appropriate changes in the ancillary ligands or the counteranion must obviously accompany any change in oxidation level to balance the charge. Examples where multiple oxidation state precurors are especially likely to be encountered include, but are not limited to, Ti(III)/Ti(IV), Fe(III)/Fe(II), and Co(III)/Co(II).

In some cases, it is advantageous for the catalyst to be attached to a solid support (by "attached to a solid support", we mean ion paired with a component on the surface, adsorbed to the surface or covalently attached to the surface). Examples of useful solid supports include: inorganic oxides, such as talcs, silicas, titania, silica/chromia, silica/chromia/titania, silica/alumina, zirconia, aluminum phosphate gels, silanized silica, silica hydrogels, silica xerogels, silica aerogels, montmorillonite clay and silica co-gels, as well as organic support materials such as polystyrene and functionalized polystyrene. (See, for example, S. B. Roscoe et al., "Polyolefin Spheres from Metallocenes Supported on Non-Interacting Polystyrene," 1998, Science, 280, 270–273 (1998)). Such supported catalysts are prepared by contacting the transition metal compound, in a substantially inert solvent (by which is meant a solvent which is either unreactive under the conditions of catalyst preparation, or if reactive, acts to usefully modify the catalyst activity or selectivity) with a solid support for a sufficient period of time to generate the supported catalyst. Examples of substantially inert solvents include toluene, o-difluorobenzene, mineral spirits, hexane, CH$_2$Cl$_2$, and CHCl$_3$.

In several cases, metal complexes are depicted herein with square planar, trigonal bipyramidal, or other coordination, however, it is to be understood that no specific geometry is implied.

Temperature and olefin pressure have significant effects on catalyst activity, and on polymer structure, composition, and molecular weight. Suitable polymerization temperatures are preferably from about 40° C. to about 100° C., more preferably 60° C. to about 90° C. Suitable polymerization pressures are preferably from about 1 bar to 200 bar, preferably 5 bar to 50 bar, more preferably 10 bar to 50 bar.

The catalysts of the present invention may be used alone, or in combination with one or more other Group 3–11 olefin polymerization or oligomerization catalysts. Such mixed catalyst systems are sometimes useful for the production of bimodal or multimodal molecular weight or compositional distributions, which may facilitate polymer processing or final product properties.

After the reaction has proceeded for a time sufficient to produce the desired polymers, the polymer can be recovered from the reaction mixture by routine methods of isolation and/or purification.

In general, the polymers of the present invention are useful as components of thermoset materials, as elastomers, as packaging materials, films, compatibilizing agents for polyesters and polyolefins, as a component of tackifying compositions, and as a component of adhesive materials.

High molecular weight resins are readily processed using conventional extrusion, injection molding, compression molding, and vacuum forming techniques well known in the art. Useful articles made from them include films, fibers, bottles and other containers, sheeting, molded objects and the like.

Low molecular weight resins are useful, for example, as synthetic waxes and they may be used in various wax coatings or in emulsion form. They are also particularly useful in blends with ethylene/vinyl acetate or ethylene/methyl acrylate-type copolymers in paper coating or in adhesive applications.

Although not required, typical pore-filling agents used in olefin or vinyl polymers may be used in the new homopolymers and copolymers of this invention. Typical pore-filling agents include pigments, colorants, titanium dioxide, carbon black, antioxidants, stabilizers, slip agents, flame retarding agents, and the like. These pore-filling agents and their use in polymer systems are known per se in the art.

Other features of the invention will become apparent in the following description of working examples, which have been provided for illustration of the invention and are not intended to be limiting thereof.

The molecular weight data presented in the following examples is determined at 135° C. in 1,2,4-trichlorobenzene using refractive index detection, calibrated using narrow molecular weight distribution poly(styrene) standards.

EXAMPLES

Example 1

Preparation of a Supported Nickel Catalyst Based on the Nickel Catalyst bbb1 bbb1

Triethylaluminum (Aldrich, 1M in hexane; 3.0 mL) was added to 0.998 g silylated silica (Crosfield, ES70YS) at 0° C., followed by 10 mL hexane. The suspension was then agitated for 3 days at room temperature. Volatiles were removed in vacuo. Another flask was then charged with the resulting solid (238 mg) and 3 mL toluene, and cooled to 0° C. A solution of bbb1 (38.3 mg) in 2 mL toluene was added. The suspension was agitated for 15 min and the solvent was removed under reduced pressure at room temperature. The color of the solid turned from red to brown. The resulting solid was used in subsequent polymerization experiments.

Example 2

Preparation of a Supported Nickel Catalyst Based on the Nickel Catalyst bbb1

Diethylzinc (Aldrich, 1M in hexane; 3.0 mL) was added to 1.00 g silylated silica (Crosfield, ES70YS) at 0° C., followed by 10 mL hexane. The suspension was then agitated for ca. 18 h at room temperature. Volatiles were removed in vacuo. Another flask was then charged with the resulting solid (215 mg) and 3 mL toluene, and cooled to 0° C. A solution of bbb1 (34.0 mg) in 2 mL toluene was added. The suspension was agitated for about 15 min and the solvent was removed under reduced pressure at room temperature. The resulting solid was used in subsequent polymerization experiments.

Example 3

Preparation of a Supported Nickel Catalyst Based on the Nickel Catalyst bbb1

Triethylborane (Aldrich, 1M in hexane; 3.0 mL) was added to 1.0 g silylated silica (Crosfield, ES70YS) at 0° C., followed by 10 mL hexane. The suspension was then agitated for ca. 18 h at room temperature. Volatiles were removed in vacuo. Another flask was then charged with the resulting solid (216 mg) and 3 mL toluene, and cooled to 0° C. A solution of bbb1 (32.3 mg) in 2 mL toluene was added. The suspension was agitated for about 15 min and the solvent was removed under reduced pressure at room temperature. The resulting solid was used in subsequent polymerization experiments.

Example 4

Preparation of a Supported Nickel Catalyst Based on the Nickel Catalyst bbb1

Triethylborane (Aldrich, 1M in hexane; 9.0 mL) was added to 1.01 g silylated silica (Crosfield, ES70YS) at 0° C., followed by 10 mL hexane. The suspension was then agitated for ca. 18 h at room temperature. Volatiles were removed in vacuo. Another flask was then charged with the resulting solid (221 mg) and 3 mL toluene, and cooled to 0° C. A solution of bbb1 (34.1 mg) in 2 mL toluene was added. The suspension was agitated for about 15 min and the solvent was removed under reduced pressure at room temperature. The resulting solid was used in subsequent polymerization experiments.

Example 5

Preparation of a Supported Nickel Catalyst Based on the Nickel Catalyst bbb1

Triethylborane (Aldrich, 1M in hexane; 3.0 mL) was added to 1.01 g dehydrated silica (Grace Davison, XPO-2402) at 0° C., followed by 10 mL hexane. The suspension was then agitated for ca. 18 h at room temperature. Volatiles were removed in vacuo. Another flask was then charged with the resulting solid (220 mg) and 3 mL toluene, and cooled to 0° C. A solution of bbb1 (33.6 mg) in 2 mL toluene was added. The suspension was agitated for about 5 min and the solvent was removed under reduced pressure at room temperature. The resulting solid was used in subsequent polymerization experiments.

Example 6

Preparation of a Supported Nickel Catalyst Based on the Nickel Catalyst bbb1

A flask was charged with dehydrated silica (Grace Davison, XPO-2402; 229 mg) and 3 mL toluene, and cooled to 0° C. A solution of bbb1 (33.5 mg) in 2 mL toluene was added. The suspension was agitated for about 5 min and the solvent was removed under reduced pressure at room temperature. The resulting solid was used in subsequent polymerization experiments.

Example 7

Preparation of a Supported Nickel Catalyst Based on the Nickel Catalyst bbb1

Trimethylaluminum (Aldrich, 2M in hexane; 1.5 mL) was added to 1.0 g sylilated silica (Crosfield ES70YS) at 0° C., followed by 10 mL hexane. The suspension was then agitated for 3 days at room temperature. Volatiles were removed in vacuo. Another flask was then charged with the resulting solid (220 mg) and 3 mL toluene, and cooled to 0° C. A solution of bbb1 (34.0 mg) in 2 mL toluene was added. The suspension was agitated for about 5 min and the solvent was removed under reduced pressure at room temperature. The resulting solid was used in subsequent polymerization experiments.

Example 8

Preparation of a Supported Nickel Catalyst Based on the Nickel Catalyst bbb1

Triethylborane (Aldrich, 1M in hexane; 6.0 mL) was added to 2.0 g silylated silica (Crosfield ES70YS) at 0° C. The suspension was then agitated for ca. 18 h at room temperature. Volatiles were removed in vacuo. Another flask was then charged with the resulting solid (494 mg) and 5 mL toluene, and cooled to 0° C. A solution of bbb1 (3.75 $\mu$mol) in 4.7 mL toluene was added. The suspension was agitated for about 5 min and the solvent was removed under reduced pressure at room temperature. The resulting solid was used in subsequent polymerization experiments.

Example 9

Preparation of a Supported Nickel Catalyst Based on the Nickel Catalyst bbb1

Triethylborane (Aldrich, 1M in hexane; 6.0 mL) was added to 2.0 g silylated silica (Crosfield ES70YS) at 0° C. The suspension was then agitated for ca. 18 h at room temperature. Volatiles were removed in vacuo. Another flask was then charged with the resulting solid (1.03 g) and 8 mL toluene, and cooled to 0° C. A solution of bbb1 (0.75 $\mu$mol) in 0.94 mL toluene was added. The suspension was agitated for about 5 min and the solvent was removed under reduced pressure at room temperature. The resulting solid was used in subsequent polymerization experiments.

Example 10

Preparation of a Supported Nickel Catalyst Based on the Nickel Catalyst bbb1

A flask was charged with MAO-treated silica (Witco TA-02794 HL-04; 217 mg) and cooled to 0° C. A solution of bbb1 (32.2 mg) in 0.4 mL toluene was added. The solvent was then removed under reduced pressure at room temperature. The resulting solid was used in subsequent polymerization experiments.

Example 11

Polymerization of Ethylene Using the Catalyst Prepared in Example 10 (Comparative)

A 1000-mL Parr® fixed-head reactor was charged with NaCl (382 g) and a catalyst delivery device containing the catalyst prepared in Example 10 (11.5 mg dispersed in 207 mg silica) was fixed to the head of the reactor. The reactor was assembled and purged five times with ethylene (ca. 50 psi). Trimethylaluminum (Aldrich, 2.0M in hexanes; 10 mL) was added to the reactor and the salt was agitated for 30 min at 85° C. The reactor was then purged three times with ethylene (200 psi). The reactor was pressurized to 300 psi $C_2H_4$ and the catalyst was then delivered while pressurizing the reactor to 600 psi $C_2H_4$. After 3.5 min, the vessel was depressurized to ca. 150 psi. Hydrogen (210 mL) was then added at t=5 min and the total pressure adjusted to 200 psi with ethylene. The reaction was allowed to proceed at an average temperature of 85° C. for 240 min. The reactor was then depressurized. The polymer was isolated by washing the content of the reactor with hot water, 6M HCl/MeOH, rinsed with methanol, and dried in a vacuum oven to give 4.17 g polymer (350 g product/g supported catalyst; 170,000 mol $C_2H_4$/mol Ni; $M_n$=81,000, $M_w/M_n$=7.9; 13 branchpoints/1000 C as determined by $^1$H NMR; $T_m$=120° C.).

Example 12 to Example 25

Polymerization of Ethylene Using Catalysts Prepared According to the Procedures Described in Example 1 to Example 9.

General Procedure Used to Obtain the Polymerization Data Given in Table I

A 1000-mL Parr® fixed-head reactor was charged with NaCl (250–450 g) and a catalyst delivery device containing a catalyst prepared according to the procedures described in Example 1 to Example 9 (0.15–0.85 $\mu$mol Ni dispersed in ca. 250 mg silica) was fixed to the head of the reactor. The reactor was assembled and purged five times with ethylene (ca. 50 psi). Trimethylaluminum (Aldrich, 2.0M in hexanes; 10 mL) was added to the reactor and the salt was agitated for 30 min at 85° C. The reactor was then purged three times with ethylene (200 psi). The catalyst was then delivered while pressurizing the reactor to 100 psi $C_2H_4$. Hydrogen (210–750 mL) was then added within 30 seconds and the total pressure adjusted to 200 psi with ethylene. The reaction was allowed to proceed at an average temperature of 85° C. for 60–240 min. The reactor was then depressurized. The polymer was isolated by washing the content of the reactor with hot water, 6M HCl/MeOH, rinsed with methanol, and dried in a vacuum oven.

TABLE I

| Example | Catalyst Source | $H_2$ (mL) | time (min) | g PE/g supported catalyst | mol $C_2H_4$/ mol Ni | $M_n$ ($\times 10^{-3}$) | $M_w/M_n$ | Branch points/ 1000 C | $T_m$ (° C.) |
|---|---|---|---|---|---|---|---|---|---|
| 12 | Example 1 | 210 | 240 | 840 | 390,000 | 78 | 2.4 | 11 | 122 |
| 13 | Example 2 | 210 | 240 | 1400 | 670,000 | 71 | 2.1 | 12 | 123 |
| 14 | Example 3 | 0 | 210 | 2400 | 1,200,000 | 367 | 4.3 | 11 | 116 |
| 15 | Example 3 | 210 | 180 | 1500 | 740,000 | 89 | 2.6 | 11 | 123 |
| 16 | Example 3 | 480 | 60 | 650 | 320,000 | 36 | 2.2 | 11 | 122 |
| 17 | Example 4 | 210 | 180 | 2200 | 1,100,000 | 119 | 2.0 | 11 | 120 |
| 18 | Example 4 | 750 | 240 | 540 | 240,000 | 28 | 2.6 | 11 | 125 |
| 19 | Example 5 | 210 | 180 | 1300 | 640,000 | 81 | 2.2 | 11 | 121 |
| 20[1] | Example 6 | 210 | 90 | 330 | 170,000 | 92 | 2.2 | 11 | 121 |
| 21 | Example 7 | 210 | 150 | 1400 | 650,000 | 74 | 2.2 | 11 | 121 |
| 22 | Example 8 | 0 | 240 | 210 | 1,000,000 | 812 | 2.4 | 11 | 118 |
| 23 | Example 8 | 210 | 180 | 92 | 430,000 | 90 | 2.8 | 12 | 123 |
| 24 | Example 9 | 0 | 210 | 15 | 710,000 | 630 | 2.1 | 9 | 118 |
| 25 | Example 9 | 210 | 60 | 3 | 147,000 | 81 | 2.8 | 11 | 121 |

[1]comparative example

Example 26

Preparation of a Mixture Containing a Supported Nickel Catalyst Based on the Nickel Catalyst bbb1

A solution of complex bbb1 (413.2 mg) in dichloromethane (6.4 mL) was added dropwise to dehydrated silica (Grace Davison; XPO-2402; 3.19 g). The solid was then place under vacuum to remove volatiles. Another flask was charged with 10.8 mg of the resulting solid and 240 mg of dehydrated silica. o-Xylene (370 mg) was then added to the mixture and the resulting solid was used in subsequent polymerization experiments.

Example 27

Polymerization of Ethylene Using Catalyst Prepared in Example 26

A 1000-mL Parr® fixed-head reactor was charged with NaCl (423 g) and a catalyst delivery device containing the catalyst mixture prepared in Example 26 (582 mg) was fixed to the head of the reactor. The reactor was assembled and purged five times with ethylene (ca. 50 psi). Trimethylaluminum (Aldrich, 2.0M in hexanes; 10 mL) was added to the reactor and the salt was agitated for 30 min at 85° C. The reactor was then purged three times with ethylene (200 psi). The catalyst was subsequently delivered while pressurizing the reactor to 100 psi $C_2H_4$. Hydrogen (210 mL) was then added within 30 seconds and the total pressure adjusted to 200 psi with ethylene. Temperature rose to 91° C. The reaction was allowed to proceed at an average temperature of 88° C. for 240 min. The reactor was then depressurized. The polymer was isolated by washing the content of the reactor with hot water, 6M HCl/MeOH, rinsed with methanol, and dried in a vacuum oven to give 8.31 g polymer (760 g product/g supported catalyst; 429,000 mol $C_2H_4$/mol Ni; $M_n$=68,000, $M_w/M_n$=2.3; 12 branchpoints/ 1000 C as determined by $^1$H NMR; $T_m$=122° C.).

Example 28

Preparation of a Supported Nickel Catalyst Based on the Nickel Catalyst bbb1

Triethylborane (Aldrich, 1M in hexane; 3.0 mL) was added to 1.0 g dehydrated silica (Grace Davison, XPO-2402) at 0° C., followed by 10 mL hexane. The suspension was then agitated for ca. 18 h at room temperature. Volatiles were removed in vacuo. Another flask was charged with bbb1 (35.0 mg) in 2 mL toluene. 1,5-Hexadiene (0.11 mL) was then added, followed by trimethylaluminum (Aldrich; 2.0M in hexane; 9.4 mL) at 0° C. The resulting solution was transferred to a flask containing 205 mg of the BEt$_3$-treated silica at 0° C. The suspension was agitated for 5 min prior to removing the volatiles in vacuo. The resulting solid was used in subsequent polymerization experiments.

Example 29

Preparation of a Supported Nickel Catalyst Based on the Nickel Catalyst bbb1

Triethylborane (Aldrich, 1M in hexane; 3.0 mL) was added to 1.0 g dehydrated silica (Grace Davison, XPO-2402) at 0° C., followed by 10 mL hexane. The suspension was then agitated for ca. 18 h at room temperature. Volatiles were removed in vacuo. Another flask was charged with bbb1 (34.6 mg) in 3 mL toluene. 1,5-Hexadiene (0.11 mL) was then added, followed by trimethylaluminum (Aldrich; 2.0M in hexane; 0.94 mL) at 0° C. The resulting solution was transferred to a flask containing a suspension of 205 mg of the BEt$_3$-treated silica in 3 mL toluene at 0° C. The suspension was agitated for 5 min prior to removing the volatiles in vacuo. The resulting solid was used in subsequent polymerization experiments.

Example 30

Polymerization of Ethylene Using Catalyst Prepared in Example 28

A 1000-mL Parr® fixed-head reactor was charged with NaCl (403 g) and a catalyst delivery device containing the catalyst prepared in Example 28 (11.6 mg dispersed in 227 mg silica) was fixed to the head of the reactor. The reactor was assembled and purged ten times with nitrogen. Trimethylaluminum (Aldrich, 2.0M in hexanes; 10 mL) was added to the reactor and the salt was agitated for 30 min at 85° C. The reactor was then purged three times with ethylene (200 psi). The catalyst was subsequently delivered while pressurizing the reactor to 200 psi $C_2H_4$. Temperature rose to 91° C. The reaction was allowed to proceed at an average temperature of 88° C. for 240 min. The reactor was then depressurized. The polymer was isolated by washing the content of the reactor with hot water, 6M HCl/MeOH, rinsed with methanol, and dried in a vacuum oven to give 10.46 g polymer (880 g product/g supported catalyst; 390,000 mol $C_2H_4$/mol Ni; $M_n$=581,000, $M_w/M_n$=1.8; 11 branchpoints/ 1000 C as determined by $^1$H NMR; $T_m$=118° C.).

Example 31

Polymerization of Ethylene Using Catalyst Prepared in Example 29

A 1000-mL Parr® fixed-head reactor was charged with NaCl (462 g) and a catalyst delivery device containing the catalyst prepared in Example 29 (10.7 mg dispersed in 188 mg silica) was fixed to the head of the reactor. The reactor was assembled and purged four times with ethylene (ca. 50 psi). Trimethylaluminum (Aldrich, 2.0M in hexanes; 10 mL) was added to the reactor and the salt was agitated for 30 min at 85° C. The reactor was then purged three times with ethylene (200 psi). The catalyst was subsequently delivered while pressurizing the reactor to 100 psi $C_2H_4$. Hydrogen (210 mL) was then added within 30 seconds and the total pressure adjusted to 200 psi with ethylene. The reaction was allowed to proceed at an average temperature of 88° C. for 210 min. The reactor was then depressurized. The polymer was isolated by washing the content of the reactor with hot water, 6M HCl/MeOH, rinsed with methanol, and dried in a vacuum oven to give 7.09 g polymer (650 g product/g supported catalyst; 290,000 mol $C_2H_4$/mol Ni; $M_n$=72,000, $M_w/M_n$=2.4; 11 branchpoints/1000 C as determined by $^1$H NMR; $T_m$=122° C.).

Example 32

Polymerization of Ethylene Using Catalyst Prepared in Example 29

A 600-mL Parr® autoclave was charged with NaCl (ca. 300 mL) and the catalyst prepared in Example 28 (25.0 mg). The reactor was assembled and pressurized to 200 psi $C_2H_4$. The reactor was heated up from room temperature to 85–90° C. within 7 min. The reaction was allowed to proceed at an average temperature of 85° C. for 67 min. The reactor was then depressurized. The polymer was isolated by washing the content of the reactor with hot water, 6M HCl/MeOH, rinsed with methanol, and dried in a vacuum oven to give 12.0 g polymer (480 g product/g supported catalyst; 214,000 mol $C_2H_4$/mol Ni; $M_n$=634,000, $M_w/M_n$=2.0; 11 branchpoints/1000 C as determined by $^1$H NMR; $T_m$=123° C.).

Example 33

Polymerization of Ethylene Using Catalyst Prepared in Example 29

A 1000-mL Parr® fixed-head reactor was charged with NaCl (354 g) and a catalyst delivery device containing the catalyst prepared in Example 29 (8.9 mg dispersed in 138 mg silica) was fixed to the head of the reactor. The reactor was assembled and purged five times with ethylene (ca. 50 psi). Trimethylaluminum (Aldrich, 2.0M in hexanes; 10 mL) was added to the reactor and the salt was agitated for 30 min at 85° C. The reactor was then purged three times with ethylene (200 psi). The catalyst was subsequently delivered while pressurizing the reactor to 200 psi $C_2H_4$. Temperature rose to 89° C. The reaction was allowed to proceed at an average temperature of 88° C. for 240 min. The reactor was then depressurized. The polymer was isolated by washing the content of the reactor with hot water, 6M HCl/MeOH, rinsed with methanol, and dried in a vacuum oven to give 8.92 g polymer (990 g product/g supported catalyst; 447,000 mol $C_2H_4$/mol Ni; $M_n$>1,000,000; 11 branchpoints/1000 C as determined by $^1$H NMR; $T_m$=116° C.).

Example 34

Preparation of a Supported Nickel Catalyst Based on the Nickel Catalyst bbb1

A solution of bbb1 (413 mg; 227 μmol) in 6.4 mL dichloromethane was added dropwise to dehydrated silica (Grace Davison, XPO-2402; 3.19 g). Volatiles were then removed in vacuo over 2 hours. A fraction of this catalyst (7.6 mg) was then dispersed in 241 mg dehydrated silica (Grace Davison, XPO-2402) and o-xylene (345 mg) was added to the mixture. The resulting mixture was used as is in subsequent polymerizations.

Example 35

Polymerization of Ethylene Using Catalyst Prepared in Example 34

A 1000-mL Parr® fixed-head reactor was charged with NaCl (378 g) and a catalyst delivery device containing the mixture prepared in Example 34 (566 mg, containing 0.45 mol Ni) was fixed to the head of the reactor. The reactor was assembled and purged five times with ethylene (ca. 50 psi). Trimethylaluminum (Aldrich, 2.0M in hexanes; 10 mL) was added to the reactor and the salt was agitated for 30 min at 85° C. The reactor was then purged three times with ethylene (200 psi). The catalyst was subsequently delivered while pressurizing the reactor to 200 psi $C_2H_4$. The reaction was allowed to proceed at an average temperature of 88° C. for 240 min. The reactor was then depressurized. The polymer was isolated by washing the content of the reactor with hot water, 6M HCl/MeOH, rinsed with methanol, and dried in a vacuum oven to give 6.83 g polymer (870 g product/g supported catalyst 491,000 mol $C_2H_4$/mol Ni; $M_n$–1,021,000, $M_w/M_n$=1.6; 11 branchpoints/1000 C as determined by $^1$H NMR; $T_m$=116° C.).

Example 36

Preparation of a Supported Nickel Catalyst Based on the Nickel Catalyst bbb1

A 200-mL flask was charged with catalyst bbb1 (38.1 mg; 20.9 μmol) and MAO-treated silica (Witco TA-02794 HL-04; 259 mg). Toluene (5 mL) was added while cooling to 0° C. After about 5 min, vacuum was applied while very gently heating the flask. The resulting solid was washed with hexane (5×20 mL) at room temperature. Trimethylaluminum (Aldrich, 2.0M in hexane; 1.0 mL) was then added at 0° C. After ca. 5 min, vacuum was applied to dryness. The resulting solid was washed with hexane (5×20 mL) at room temperature, and dried in vacuo. The catalyst was stored at −30° C. until used in subsequent polymerization.

Example 37

Polymerization of Ethylene Using Catalyst Prepared in Example 36

A 600-mL Parr® autoclave was charged with the catalyst prepared in Example 36 (60.8 mg) under $N_2$. The reactor was assembled and hexane (220 mL), pretreated with MAO-treated silica (Witco TA-02794 HL-04), was added to the reactor. The suspension was agitated vigorously. The reactor was then pressurized to 150 psi with $C_2H_4$, while heating to 75° C. Once the desired temperature was reached (<3 min), ethylene was added to reach a total reactor pressure of 200 psi. The reaction was allowed to proceed for 120 min at 75° C. Pressure was then released and the resulting solid filtered, washed with acetone, and dried in a vacuum oven to yield 6.48 g polymer (110 g PE/g supported catalyst; 53,000 mol $C_2H_4$/mol Ni; $M_n$>1,000,000; 10 branchpoints/1000 C as determined by $^1$H NMR; $T_m$=121° C.).

Example 38

Polymerization of Ethylene Using Catalyst Prepared in Example 36

A 600-mL Parr® autoclave was charged with the catalyst prepared in Example 36 (50.0 mg) under $N_2$. The reactor was assembled and hexane (220 mL), pretreated with MAO-treated silica (Witco TA-02794 IIL-04), was added to the reactor. The suspension was agitated vigorously. The reactor was then pressurized to 60 psi with $C_2H_4$. Hydrogen (4 psi) was then added and the reactor immediately pressurized to 150 psi with $C_2H_4$ while heating to 75° C. Once the desired temperature was reached (<3 min), ethylene was added to reach a total reactor pressure of 200 psi. The reaction was allowed to proceed for 120 min at 75° C. Pressure was then released and the resulting solid filtered, washed with acetone, and dried in a vacuum oven to yield 4.24 g polymer (85 g PE/g supported catalyst; 42,000 mol $C_2H_4$/mol Ni; $M_n$=57,600, $M_w/M_n$=2.4; 10 branchpoints/1000 C as determined by $^1$H NMR; $T_m$=125° C.).

Example 39

Polymerization of Ethylene Using Catalyst Prepared in Example 4

A 1000-mL Parr® fixed-head reactor was charged with NaCl (392 g) and a catalyst delivery device containing a catalyst prepared according to the procedures described in Example 4 (5.8 mg dispersed in 135 mg silica) was fixed to the head of the reactor. The reactor was assembled and purged five times with ethylene (ca. 50 psi). Trimethylaluminum (Aldrich, 2.0M in hexanes; 10 mL) was added to the reactor and the salt was agitated for 30 min at 75° C. The reactor was then purged three times with ethylene (200 psi). The catalyst was then delivered while pressurizing the reactor to ca. 100 psi $C_2H_4$. Hydrogen (420 mL) was then added within 10 seconds and the total pressure adjusted to 200 psi with ethylene. The reaction was allowed to proceed at an average temperature 74° C. for 240 min. The reactor was then depressurized. The polymer was isolated by washing the content of the reactor with hot water, 6M HCl/MeOH, rinsed with methanol, and dried in a vacuum oven to give 8.92 g of material (1520 g PE/g supported catalyst; 733,000 mol $C_2H_4$/mol Ni; $M_n$=110,000, $M_w/M_n$=2.8; 8 branchpoints/1000 C as determined by $^1$H NMR; $T_m$=124° C.).

Example 40

Polymerization of Ethylene Using Catalyst Prepared in Example 4

A 1000-mL Parr® fixed-head reactor was charged with NaCl (407 g) and a catalyst delivery device containing a catalyst prepared according to the procedures described in Example 4 (5.6 mg dispersed in 130 mg silica) was fixed to the head of the reactor. The reactor was assembled and purged five times with ethylene (ca. 50 psi). Trimethylaluminum (Aldrich, 2.0M in hexanes; 10 mL) was added to the reactor and the salt was agitated for 30 min at 75° C. The reactor was then purged three times with ethylene (200 psi). The catalyst was then delivered while pressurizing the reactor to ca. 100 psi $C_2H_4$. Hydrogen (210 mL) was then added within 30 seconds and the total pressure adjusted to 200 psi with ethylene. The reaction was allowed to proceed at an average temperature 75° C. for 240 min. The reactor was then depressurized. The polymer was isolated by washing the content of the reactor with hot water, 6M HCl/MeOH, rinsed with methanol, and dried in a vacuum oven to give 17.0 g of material (3010 g PE/g supported catalyst; 1,450,000 mol $C_2H_4$/mol Ni; $M_n$=89,000, $M_w/M_n$=2.5; 10 branchpoints/1000 C as determined by $^1$H NMR; $T_m$=124° C.).

Example 41

Preparation of a Supported Nickel Catalyst Based on the Nickel Catalyst bbb1

A 200-mL flask was charged with MAO-treated silica (Witco TA-02794 HL-04; 444 mg) and cooled to 0° C. A solution of the nickel catalyst bbb1 in toluene (3 mL) was added. After about 5 min, volatiles were removed in vacuo. The resulting solid was washed with hexane (2×20 mL and 2×10 mL) at room temperature. Triethylborane (Aldrich, 1.0M in hexane; 1.5 mL) was then added at 0° C. After ca. 10 min, vacuum was applied to dryness. The catalyst was stored at −30° C. until used in subsequent polymerization.

Example 42

Polymerization of Ethylene Using Catalyst Prepared in Example 41

A 1000-mL Parr® fixed-head reactor was charged with NaCl (394 g) and a catalyst delivery device containing a catalyst prepared according to the procedures described in Example 41 (12.2 mg dispersed in 135 mg silica) was fixed to the head of the reactor. The reactor was assembled and purged five times with ethylene (ca. 50 psi). Trimethylaluminum (Aldrich, 2.0M in hexanes; 10 mL) was added to the reactor and the salt was agitated for 30 min at 85° C. The reactor was then purged three times with ethylene (200 psi). The catalyst was then delivered while pressurizing the reactor to 200 psi $C_2H_4$. The reaction was allowed to proceed at an average temperature 89° C. for 210 min. The reactor was then depressurized. The polymer was isolated by washing the content of the reactor with hot water, 6M HCl/MeOH, rinsed with methanol, and dried in a vacuum oven to give 16.3 g of material (1320 g product/g supported catalyst; $M_n$=768,000, $M_w/M_n$=1.3; 14 branchpoints/1000 carbons as determined by $^1$H NMR; $T_m$=114° C.).

Example 43

Polymerization of Ethylene Using Catalyst Prepared in Example 41

A 1000-mL Parr® fixed-head reactor was charged with NaCl (418 g) and a catalyst delivery device containing a catalyst prepared according to the procedures described in Example 41 (12.2 mg dispersed in 135 mg silica) was fixed to the head of the reactor. The reactor was assembled and purged five times with ethylene (ca. 50 psi). Trimethylaluminum (Aldrich, 2.0M in hexanes; 10 mL) was added to the reactor and the salt was agitated for 30 min at 85° C. The reactor was then purged three times with ethylene (200 psi). The catalyst was then delivered while pressurizing the reactor to ca. 100 psi $C_2H_4$. Hydrogen (210 mL) was then added within 30 seconds and the total pressure adjusted to 200 psi with ethylene. The reaction was allowed to proceed at an average temperature 87° C. for 240 min. The reactor was then depressurized. The polymer was isolated by washing the content of the reactor with hot water, 6M HCl/MeOH, rinsed with methanol, and dried in a vacuum oven to give 13.3 g of material (1080 g product/g supported catalyst; $M_n$=130,000, $M_w/M_n$=3.2; 12 branchpoints/1000 carbons as determined by $^1$H NMR; $T_m$=119° C.).

Example 44

Polymerization of Ethylene Using Catalyst Prepared in Example 41

A 1000-mL Parr® fixed-head reactor was charged with NaCl (397 g) and a catalyst delivery device containing a catalyst prepared according to the procedures described in Example 41 (14.3 mg dispersed in 192 mg silica) was fixed to the head of the reactor. The reactor was assembled and purged five times with ethylene (ca. 50 psi). Trimethylaluminum (Aldrich, 2.0M in hexanes; 10 mL) was added to the reactor and the salt was agitated for 30 min at 75° C. The reactor was then purged three times with ethylene (200 psi). The catalyst was then delivered while pressurizing the reactor to ca. 100 psi $C_2H_4$. Hydrogen (210 mL) was then added within 30 seconds and the total pressure adjusted to 200 psi with ethylene. The reaction was allowed to proceed at an average temperature 76° C. for 240 min. The reactor was then depressurized. The polymer was isolated by washing the content of the reactor with hot water, 6M HCl/MeOH, rinsed with methanol, and dried in a vacuum oven to give 17.1 g of material (1180 g product/g supported catalyst; $M_n$=76,000, $M_w/M_n$=2.7; 11 branchpoints/1000 carbons as determined by $^1H$ NMR; $T_m$=123° C.).

Example 45

Polymerization of Ethylene Using Catalyst Prepared in Example 3

A 1000-mL Parr® fixed-head reactor was charged with NaCl (477 g) and a catalyst delivery device containing a catalyst prepared according to the procedures described in Example 3 (7.3 mg dispersed in 118 mg silica) was fixed to the head of the reactor. The reactor was assembled and purged five times with ethylene (ca. 50 psi). Trimethylaluminum (Aldrich, 2.0M in hexanes; 10 mL) was added to the reactor and the salt was agitated for 30 min at 70° C. The reactor was then purged three times with ethylene (200 psi). The catalyst was then delivered while pressurizing the reactor to ca. 100 psi $C_2H_4$. Hydrogen (210 mL) was then added within 30 seconds and the total pressure adjusted to 200 psi with ethylene. The reaction was allowed to proceed at an average temperature 71° C. for 240 min. The reactor was then depressurized. The polymer was isolated by washing the content of the reactor with hot water, 6M HCl/MeOH, rinsed with methanol, and dried in a vacuum oven to give 8.21 g of material (1110 g product/g supported catalyst; 550,000 mol $C_2H_4$/mol Ni; $M_n$=101,000, $M_w/M_n$=3.0; 9 branchpoints/1000 carbons as determined by $^1H$ NMR; $T_m$=128° C.).

Example 46

Synthesis of the Nickel Complex bbb1 aaa15

Example 47

In an argon filled glove box, aaa15, (98.0 mg, 0.100 mmol; prepared according to procedures similar to those described in WO 00/50470), nickel(II)acetonylacetonate (25.7 mg, 0.100 mmol), and triphenylcarbenium tetrakis (pentafluorophenyl)borate (92.3 mg, 0.100 mmol) were weighed to a Schlenk flask. On the Schlenk line, 10 mL dry diethyl ether was added to give a dark red solution. Dry hexane (4 mL) was added and dark crystals separated. The supernatant was removed via filer paper-tipped cannula. The dark bronze crystals were washed (2×10 mL) with a.hexane/ether (1/1) mixture, then dried several hours in vacuo to afford 163.3 mg (89%) bbb1.

Example 48

Preparation of a Supported Nickel Catalyst Based on aa1 aa1

Complex aa1 (73.6 mg) was place in a vial under nitrogen and dissolved in 0.75 mL dichloromethane. The resulting solution was added dropwise to dehydrated silica (Grace Davison, XPO-2402; 0.50 g) with appropriate agitation, at 0° C. The volatiles were then removed in vacuo to give the desired product, used in subsequent polymerization experiments.

Example 49

Polymerization of Ethylene in the Presence of Hydrogen Using the Catalyst Prepared in Example 48

Figure 1:
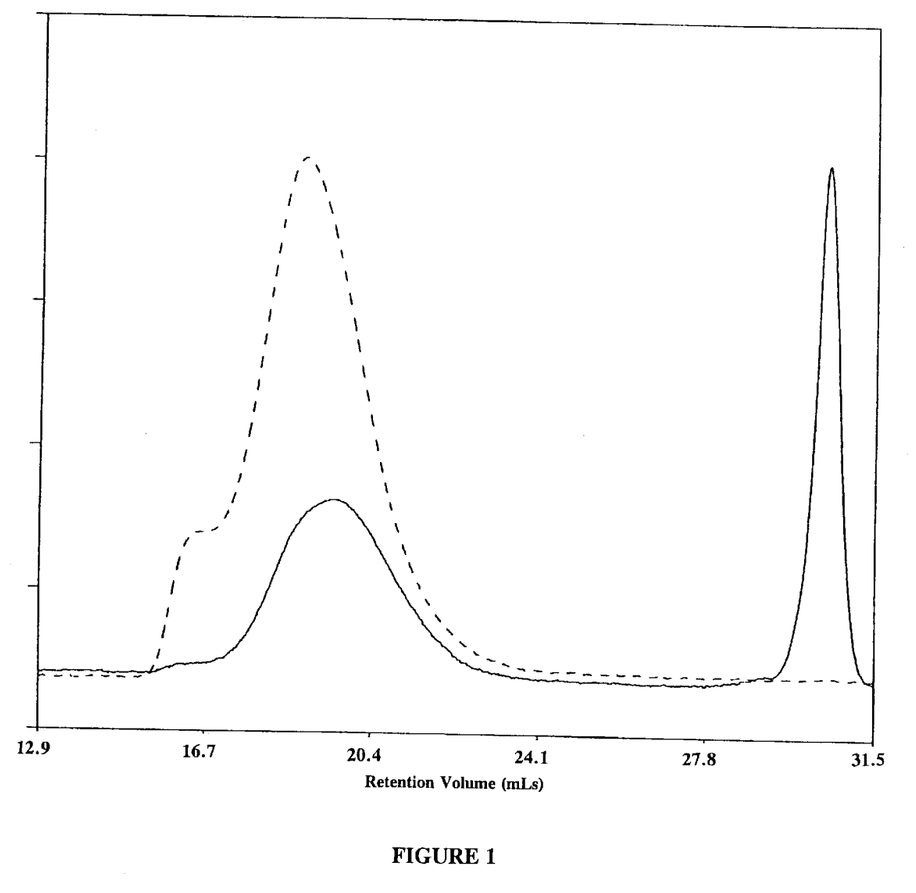
FIG. 1 is a GPC curve of the polymer prepared in Example 49.

A 1000-mL Parr® fixed-head reactor was charged with NaCl (324 g) and a catalyst delivery device containing the catalyst prepared in Example 48 (7.0 mg dispersed in 160 mg XPO-2402 silica) was fixed to the head of the reactor. The reactor was assembled and purged five times with nitrogen (ca. 40 psi). Trimethylaluminum (Aldrich, 2.0M in hexanes; 10 mL) was added to the reactor and the salt was agitated for 30 min at 85° C. The reactor was then purged three times with ethylene (200 psi). Hydrogen (100 mL) was then added via a hypodermic syringe and the catalyst delivered while pressurizing the reactor to 200 psi $C_2H_4$. The reaction was allowed to proceed for 105 min at 85° C. The reactor was then depressurized. The polymer was isolated by washing the content of the reactor with hot water, 6M HCl/MeOH, rinsed with methanol, and dried in a vacuum oven to give 0.67 g polymer (73 g product/g supported catalyst; $M_n$=127,000, $M_w/M_n$=3.6 (GPC trace shown in FIG. 1); 13.9 branchpoints/1000 carbons as determined by $^1H$ NMR).

Example 50

Polymerization of Ethylene in the Presence of Hydrogen Using the Catalyst Prepared in Example 48

Figure 2:
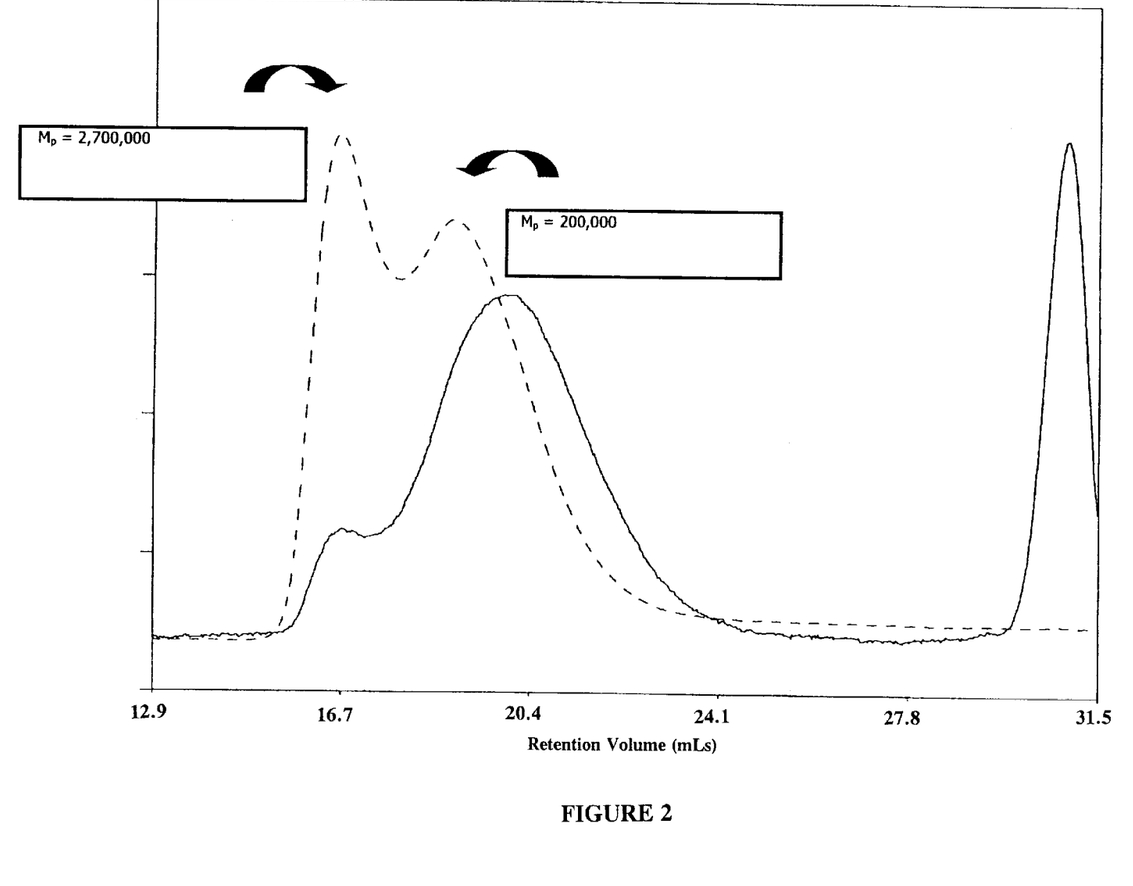
FIG. 2 is a GPC curve of the polymer prepared in Example 50.

A 1000-mL Parr® fixed-head reactor was charged with NaCl (350 g) and a catalyst delivery device containing the catalyst prepared in Example 48 (5.5 mg dispersed in 148 mg XPO-2402 silica) was fixed to the head of the reactor. The reactor was assembled and purged five times with nitrogen (ca. 40 psi). Trimethylaluminum (Aldrich, 2.0M in hexanes; 10 mL) was added to the reactor and the salt was agitated for 30 min at 85° C. The reactor was then purged three times with ethylene (200 psi). The catalyst was then delivered while pressurizing the reactor to 200 psi $C_2H_4$. After 1 min at 200 psi $C_2H_4$, the reactor was slowly depressurized over 90 sec. Hydrogen (100 mL) was then added via a hypodermic syringe and the reactor repressurized to 200 psi $C_2H_4$. The reaction was allowed to proceed for 120 min at 85° C. The reactor was then depressurized. The polymer was isolated by washing the content of the reactor with hot water, 6M HCl/MeOH, rinsed with methanol, and dried in a vacuum oven to give 2.0 g polymer (340 g product/g supported catalyst; $M_n$=81,600, $M_w/M_n$=3.7 (GPC trace shown in FIG. 2); 12.4 branchpoints/1000 carbons as determined by $^1$H NMR; $T_m$=122° C.).

Example 51

Polymerization of Ethylene in the Presence of Hydrogen Using the Catalyst Prepared in Example 48

A 1000-mL Parr® fixed-head reactor was charged with NaCl (372 g) and a catalyst delivery device containing the catalyst prepared in Example 48 (6.2 mg dispersed in 162 mg XPO-2402 silica) was fixed to the head of the reactor. The reactor was assembled and purged five times with nitrogen (ca. 40 psi). Trimethylaluminum (Aldrich, 2.0M in hexanes; 10 mL) was added to the reactor and the salt was agitated for 30 min at 85° C. The reactor was then purged three times with ethylene (200 psi). The catalyst was then delivered while pressurizing the reactor to 200 psi $C_2H_4$. After 30 min at 200 psi $C_2H_4$, the reactor was slowly depressurized and hydrogen (100 mL) was added via a hypodermic syringe. The reactor was then repressurized to 200 psi $C_2H_4$ and the reaction allowed to proceed for 210 min at 85° C. The reactor was then depressurized. The polymer was isolated by washing the content of the reactor with hot water, 6M HCl/MeOH, rinsed with methanol, and dried in a vacuum oven to give 4.4 g polymer (690 g product/g supported catalyst; $M_n$=70,100, $M_w/M_n$=8.4; 15.8 branchpoints/1000 carbons as determined by $^1$H NMR; $T_m$=109° C.).

Example 52

Polymerization of Ethylene in the Presence of Hydrogen Using the Catalyst Prepared in Example 48

A 1000-mL Parr® fixed-head reactor was charged with NaCl (303 g) and a catalyst delivery device containing the catalyst prepared in Example 48 (15.7 mg dispersed in 188 mg XPO-2402 silica) was fixed to the head of the reactor. The reactor was assembled and purged five times with nitrogen (ca. 40 psi). Trimethylaluminum (Aldrich, 2.0M in hexanes; 10 mL) was added to the reactor and the salt was agitated for 30 min at 85° C. The reactor was then purged three times with ethylene (200 psi). Hydrogen (16 psi) was then added and the catalyst delivered while pressurizing the reactor to 600 psi $C_2H_4$. The reaction was allowed to proceed for 60 min at 85° C. The reactor was then depressurized. The polymer was isolated by washing the content of the reactor with hot water, 6M HCl/MeOH, rinsed with methanol, and dried in a vacuum oven to give 9.5 g polymer (590 g product/g supported catalyst; $M_n$=32,200, $M_w/M_n$=3.5; 10.1 branchpoints/1000 carbons as determined by $^1$H NMR; $T_m$=124° C.).

Example 53

Polymerization of Ethylene Using a Catalyst Prepared as in Example 6 (comparative)

A 1000-mL Parr® fixed-head reactor was charged with NaCl (382 g) and a catalyst delivery device containing a catalyst prepared as in Example 10 (but where 68 mg bbb1 and 436 mg XPO-2402 was used) (11.5 mg dispersed in 207 mg silica) was fixed to the head of the reactor. The reactor was assembled and purged five times with ethylene (ca. 50 psi). Trimethylaluminum (Aldrich, 2.0M in hexanes; 10 mL) was added to the reactor and the salt was agitated for 30 min at 85° C. The reactor was then purged three times with ethylene (200 psi). The catalyst was then delivered while pressurizing the reactor to 200 psi $C_2H_4$. The reaction was allowed to proceed at an average temperature of 85° C. for 240 min. The reactor was then depressurized. The polymer was isolated by washing the content of the reactor with hot water, 6M HCl/MeOH, rinsed with methanol, and dried in a vacuum oven to give 11.5 g polymer (1900 g product/g supported catalyst; 890,000 mol $C_2H_4$/mol Ni; $M_n$=402,000, $M_w/M_n$=6.9; 15 branchpoints/1000 carbons as determined by $^1$H NMR; $T_m$=112° C.).

Example 54

Preparation of a Supported Nickel Catalyst Based on the Nickel Catalyst bbb1

A flask was charged with silylated silica (Crosfield, ES70YS; 232 mg) and cooled to 0° C. A solution of bbb1 (33.5 mg) in 1.5 mL toluene was added. The original vial containing bbb1 was washed with additional (1.5 mL) toluene, and added to the silica. The suspension was agitated for about 5 min and the solvent was removed under reduced pressure at room temperature over 2 h. The resulting solid was used in subsequent polymerization experiments.

Example 55

Polymerization of Ethylene Using the Catalysts Prepared According to the Procedures Described in Example 54 (Comparative)

A 1000-mL Parr® fixed-head reactor was charged with NaCl (324 g) and a catalyst delivery device containing a catalyst prepared according to the procedures described in Example 54 (21.3 mg dispersed in 233 mg silica) was fixed to the head of the reactor. The reactor was assembled and purged under a continuous flow of nitrogen for 60 min. Trimethylaluminum (5.2M in toluene; 1.0 mL) was added to the reactor. The catalyst was then delivered while pressurizing the reactor to 100 psi $C_2H_4$. Hydrogen (210 mL) was then added within 30 seconds and the total pressure adjusted to 200 psi with ethylene. The reaction was allowed to proceed at an average temperature of 87° C. for 240 min. The reactor was then depressurized. The polymer was isolated by washing the content of the reactor with hot water, 6M HCl/MeOH, rinsed with methanol, and dried in a vacuum oven to give 4.48 g polymer (390 g product/g supported catalyst; 200,000 mol $C_2H_4$/mol Ni; $M_n$=71,000, $M_w/M_n$=3.0; 11 branchpoints/1000 carbons as determined by $^1$H NMR; $T_m$=123° C.).

Example 56

Polymerization of Ethylene Using the Catalysts Prepared According to the Procedures Described in Example 54 (Comparative)

A 1000-mL Parr® fixed-head reactor was charged with NaCl (379 g) and a catalyst delivery device containing a catalyst prepared according to the procedures described in Example 54 (21.1 mg dispersed in 230 mg silica) was fixed to the head of the reactor. The reactor was assembled and purged under a continuous flow of nitrogen for 60 min. Trimethylaluminum (5.2M in toluene; 1.0 mL) was added to the reactor. The catalyst was then delivered while pressurizing the reactor to 200 psi $C_2H_4$. The reaction was allowed to proceed at an average temperature of 85° C. for 270 min. The reactor was then depressurized. The polymer was isolated by washing the content of the reactor with hot water, 6M HCl/MeOH, rinsed with methanol, and dried in a vacuum oven to give 47 g polymer (2200 g product/g supported catalyst; 1,500,000 mol $C_2H_4$/mol Ni; $M_n$>1,500,000; 12 branchpoints/1000 carbons as determined by $^1$H NMR; $T_m$=112° C.).

Example 56

Preparation of a Supported Nickel Catalyst Based on the Nickel Catalyst bbb1

Triethylborane (Aldrich, 1M in hexane; 3.0 mL) was added to 1.0 g silylated silica (Crosfield, ES70YS) at 0° C., followed by 10 mL hexane. The suspension was then agitated for ca. 18 h at room temperature. Volatiles were removed in vacuo. Another flask was then charged with the resulting solid (228 mg) and 3 mL toluene, and cooled to 0° C. A solution of bbb1 (22.7 mg) in 2 mL toluene was added. The suspension was agitated for about 5 min and the solvent was removed under reduced pressure at room temperature. The resulting solid was used in subsequent polymerization experiments.

Example 57

Polymerization of Ethylene Using Catalysts Prepared According to the Procedures Described in Example 56

A 1000-mL Parr® fixed-head reactor was charged with NaCl (403 g) and a catalyst delivery device containing a catalyst prepared according to the procedures described in Example 56 (7.8 mg dispersed in 186 mg silica) was fixed to the head of the reactor. The reactor was assembled and evacuated/purged three times with nitrogen. Trimethylaluminum (Aldrich, 2.0M in hexanes; 10 mL) was added to the reactor and the salt was agitated for 50 min at 85° C. The reactor was then purged three times with ethylene (200 psi). Hydrogen (210 mL) was added to the reactor while pressuring it to 100 psi with ethylene. The catalyst was then delivered while further increasing the reactor pressure to 200 psi with $C_2H_4$. The reaction was allowed to proceed at an average temperature of 88° C. for 120 min. The reactor was then depressurized. The polymer was isolated by washing the content of the reactor with hot water, 6M HCl/MeOH, rinsed with methanol, and dried in a vacuum oven to give 7.18 g product (900 g product/g supported catalyst; 640 mol $C_2H_4$/mol Ni; $M_n$=75,000, $M_w/M_n$=2.3; 11 branchpoints/1000 carbons as determined by $^1$H NMR; $T_m$=121 C).

Example 58

Polymerization of Ethylene Using the Nickel Complex bbb1

A 600-mL Parr® reactor was charged with 300 mL hexane and $BEt_3$ (Aldrich, 1.0M in hexane; 1.0 mL) under argon. The reactor was pressurized and depressurized three times with ethylene (ca. 100 psi). Hydrogen (16 psi) was then added. The reactor was pressurized with to about 100 psi with ethylene and then heated to 70° C. Once the temperature stabilized, the nickel complex bbb1 (1.4 μmol) was then added via an injection loop while further pressurizing the reactor with ethylene to 200 psi. No ethylene uptake was observed. The temperature was then ramped up to 85° C. No ethylene uptake was observed. The reaction was quenched with acetone at 60 min. No polymer was isolated.

We claim:

1. A process for the polymerization of olefins, comprising: contacting one or more olefins with a catalyst comprising a Group 8–10 transition metal complex of a bidentate N,N—, N,O—, N,P—, or P,P-donor ligand, wherein the catalyst is attached to a solid support which has been treated with a pore-filling agent, either before, during or after the catalyst and the support have been combined, and wherein the catalyst comprises a nickel complex of a bidentate N,N-donor ligand, wherein the N-donor atoms are substituted by aromatic or heteroaromatic rings, and wherein the ortho positions of the rings are substituted by bromo, trifluoromethyl, fluoroalkyl, aryl, or heteroaryl groups.

2. A process for the polymerization of olefins, comprising: contacting one or more olefins with a catalyst comprising a Group 8–10 transition metal complex of a bidentate N,N—, N,O—, N,P—, or P,P-donor ligand, wherein the catalyst is attached to a solid support which has been treated with a pore-filling agent, either before, during or after the catalyst and the support have been combined, and wherein at least 20% of the remaining pore volume of the supported catalyst is filled by the pore-filling agent.

3. A process for the polymerization of olefins, comprising: contacting one or more olefins with a catalyst comprising a Group 8–10 transition metal complex of a bidentate N,N—, N,O—, N,P—, or P,P-donor, wherein the catalyst is attached to a solid support, wherein the catalyst is first activated in the absence of hydrogen in a first reactor containing one or more olefins, and then introduced into a second reactor containing hydrogen in which the bulk of the polymerization takes place, and wherein the catalyst comprises a nickel complex of a bidentate N,N-donor ligand, wherein the N-donor atoms are substituted by aromatic or heteroaromatic rings, and wherein the ortho positions of the rings are substituted by bromo, trifluoromethyl, fluoroalkyl, aryl, or heteroaryl groups.

4. The process according to claim 3, wherein two or three of the ortho positions of said rings are substituted by aryl or heteroaryl groups, and the remainder of the ortho positions are substituted by bromo, trifluoromethyl, or fluoroalkyl groups.

5. A process for the polymerization of olefins, comprising: contacting one or more olefins with a catalyst comprising a Group 8–10 transition metal complex of a bidentate N,N—, N,O—, N,P—, or P,P-donor, wherein the catalyst is attached to a solid support, and wherein the catalyst is first activated in the presence of hydrogen at a partial pressure of ethylene of at least 600 psig.

6. The process according to claim 2, wherein at least 40% of the remaining pore volume of the supported catalyst is filled by the pore-filling agent.

7. The process according to claim 2, wherein at least 60% of the remaining pore volume of the supported catalyst is filled by the pore-filling agent.

* * * * *